United States Patent [19]

Ravichandran et al.

[11] Patent Number: 5,118,736

[45] Date of Patent: Jun. 2, 1992

[54] N,N-BIS(1-HYDROCARBYLOXY-2,2,6,6-TETRAMETHYLPIPERIDIN-4-YL)AMINO TRIAZINES AND STABILIZED COMPOSITIONS

[75] Inventors: Ramanathan Ravichandran, Nanuet; James P. Galbo, Hartsdale, both of N.Y.

[73] Assignee: Ciba-Geigy Corporation, Ardsley, N.Y.

[21] Appl. No.: 727,340

[22] Filed: Jul. 3, 1991

Related U.S. Application Data

[63] Continuation of Ser. No. 479,906, Feb. 14, 1990, abandoned, which is a continuation-in-part of Ser. No. 326,847, Mar. 21, 1989, abandoned.

[51] Int. Cl.$^5$ ................................................. C08K 5/34
[52] U.S. Cl. ................................. 524/100; 544/198; 544/209; 544/212
[58] Field of Search ................ 524/100; 544/198, 209, 544/212

[56] References Cited

.U.S. PATENT DOCUMENTS

| | | | |
|---|---|---|---|
| 4,263,434 | 4/1981 | Cassandrini et al. | 524/100 |
| 4,344,876 | 8/1982 | Berner | 524/91 |
| 4,356,287 | 10/1982 | Loffelman et al. | 525/204 |
| 4,426,471 | 1/1984 | Berner | 524/91 |
| 4,426,472 | 1/1984 | Berner | 524/99 |
| 4,533,688 | 8/1985 | Nakahara et al. | 524/100 |
| 4,698,381 | 10/1987 | Minagawa et al. | 544/198 |
| 4,703,073 | 10/1987 | Winter et al. | 524/99 |
| 4,740,544 | 4/1988 | Nakahara et al. | 524/100 |
| 4,760,141 | 7/1988 | Nakahara et al. | 524/100 |
| 4,816,507 | 3/1989 | Cantatore et al. | 524/100 |
| 4,906,678 | 3/1990 | Cantatore et al. | 524/100 |
| 4,910,238 | 3/1990 | Makahara et al. | 524/100 |
| 4,948,889 | 8/1990 | Cantatore et al. | 524/100 |
| 4,997,938 | 3/1991 | Cantatore et al. | 524/100 |

OTHER PUBLICATIONS

Chem. Abst. 101, 92187w; WPI 84-116091/19.
T. Kurumada et al., J. Polym. Sci., Polym. Chem. Ed., 22, 277(1984).
Chem. Abst. 106, 139325k; WPI 87-015865/03.
Derwent Abst. 88-316617/45.
Shlyapintokh et al., "Developments in Polymer Stabilisation", V, 41-70, (1982).

*Primary Examiner*—Kriellion S. Morgan
*Attorney, Agent, or Firm*—Luther A. R. Hall

[57] ABSTRACT

Triazines substituted with an N,N-bis(1-hydrocarbyloxy-2,2,6,6-tetramethylpiperidin-4-yl)amino moiety are effective stabilizers for polymer compositions against the deleterious effects of actinic light.

18 Claims, No Drawings

N,N-BIS(1-HYDROCARBYLOXY-2,2,6,6-TETRAMETHYLPIPERIDIN-4-YL)AMINO TRIAZINES AND STABILIZED COMPOSITIONS

This application is a continuation of application Ser. No. 479,906, filed Feb. 14, 1990, which is a continuation-in-part of Ser. No. 326,847, filed Mar. 21, 1989, now abandoned.

The instant invention pertains to s-triazine moieties substituted by an N,N-bis(1-hydrocarbyloxy-2,2,6,6-tetramethylpiperidin-4-yl)amino groups which material is an effective stabilizer for protecting polymers from the deleterious effects of actinic light.

BACKGROUND OF THE INVENTION

Hindered amine light stabilizers containing triazine moieties are known in the art as seen in European Patent applications Nos. 107,615; and 209,127; and U.S. Pat. Nos. 4,533,688, 4,740,544, 4,356,287 and 4,760,141.

DETAILED DISCLOSURE

The instant invention pertains to compounds having formula I, II or III

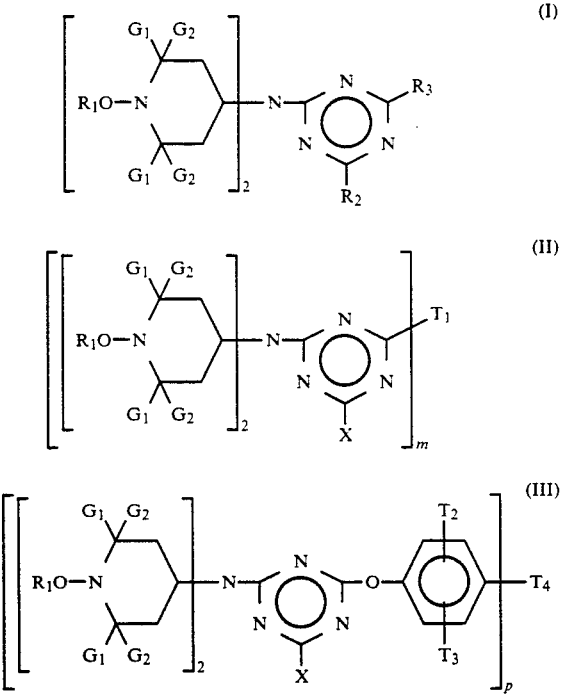

wherein $G_1$ and $G_2$ are independently alkyl of 1 to 4 carbon atoms, or $G_1$ and $G_2$ together are pentamethylene, $R_1$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl.

$R_2$ and $R_3$ are independently —$SR_5$, —$NR_6R_7$, —$NR_8$—$R_9$—$NR_{10}R_{11}$, —$OR_4$, —$O(-R_{12}O)_nR_{13}$,

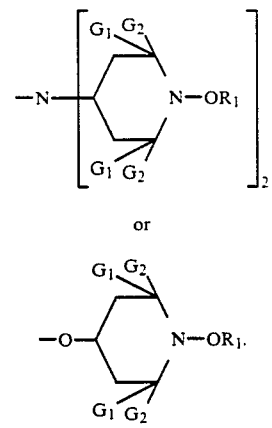

$R_4$ has the same meaning as $R_1$, $R_5$ has the same definitions as $R_1$ and additionally $R_5$ is alkyl of 2 to 4 carbon atoms substituted by hydroxy, by alkoxy of 1 to 12 carbon atoms or by di($C_1$-$C_4$-alkyl)amino, $R_6$ and $R_8$ are independently hydrogen, alkyl of 1 to 18 carbon atoms, cycloalkyl of 5 to 12 carbon atoms, aralkyl of 7 to 15 carbon atoms or alkyl of 2 to 4 carbon atoms substituted by hydroxy, by alkoxy of 1 to 12 carbon atoms or by

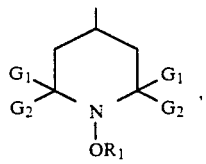

$R_7$ has the same meaning as $R_6$ or $R_6$ and $R_7$ together with N-atom to which they are linked for a 5-7- membered heterocyclic ring containing one or two nitrogen atoms or oxygen, $R_9$ is alkylene of 2 to 12 carbon atoms, $R_{10}$ and $R_{11}$ have independently of the same definition as $R_6$ or $R_{10}$ and $R_{11}$ together have the same definition as $R_6$ and $R_7$ together.

$R_{12}$ is alkylene of 2 to 4 carbon atoms, $R_{13}$ is hydrogen, alkyl of 1 to 18 carbon atoms, phenyl or said phenyl substituted by alkyl of 1 to 12 carbon atoms or by

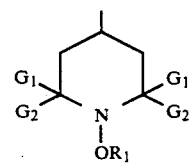

n is an integer of 2 to 20,
m is an integer of 2 to 4,
X has the same meanings as $R_2$,
$T_1$ is piperazinyl,
—$NR_{14}$—$(CH_2)_aO(CH_2)_bO(CH_2)_aNR_{14}$—, —$NR_{14}$—$(CH_2)_d$—$NR_{24}$— or —$NH$—$(CH_2)_a$—$N$—$(CH_2)_b$—$N[(CH_2)_c$—$N]_fH$— wherein $R_{14}$ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, a, b, c, d are independently 2 or 3, f is 0 or 1, $T_2$ and $T_3$ are independently hydrogen or alkyl of 1 to 6 carbon atoms, $T_4$ is a direct bond or a hydrocarbyl group of valence p, and p is 2 or 3, with the proviso that when the compound is of formula I or of formula III, $R_1$ is not alkyl.

Preferably $G_1$ and $G_2$ are each methyl.

$R_1$ is preferably alkyl of 1 to 12 carbon atoms, cyclohexyl or alpha-methylbenzyl; most preferably methyl, heptyl, octyl, nonyl, cyclohexyl or alpha-methylbenzyl.

Preferably $R_2$ and $R_3$ are the same and are —$SR_5$, —$NR_6R_7$, or

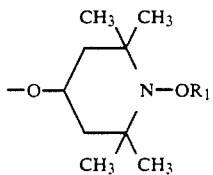

$R_5$ is preferably alkyl of 1 to 18 carbon atoms.

$R_6$ is preferably hydrogen, alkyl of 1 to 18 carbon atoms, or a group

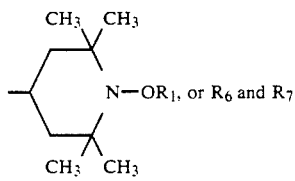

together with the nitrogen atom to which they are attached are morpholino, $T_1$ is preferably

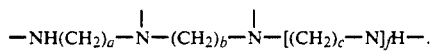

$T_4$ is preferably a direct bond or alkylidene of 2 to 4 carbon atoms.

The instant compounds are prepared by conventional methods using cyanuric chloride, substituted chloro-s-triazine derivatives with the appropriate amine or other reactant.

The reaction is conveniently carried out in inert solvents such as acetone, methyl ethyl ketone, dioxane, benzene, toluene, tetrahydrofuran, xylene and the like in the presence of an organic or inorganic base preferably sodium or potassium hydroxide or carbonate in quantities equivalent to the hydrochloric acid produced in the replacement reaction.

Another method involves the preparation of the N-hydrocarbyloxy compounds directly from the hindered amine s-triazine precursors using aqueous tert-butyl hydroperoxide, molybdenum trioxide in an appropriate hydrocarbon medium.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

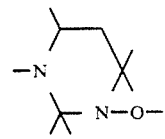

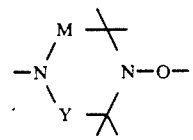

wherein M and Y are independently methylene or carbonyl, preferably M being methylene and Y being carbonyl. It is understood that the identified substituents applicable to such compounds are those which are appropriate for substitution on the ring nitrogen atoms.

The intermediates used to make the instant compounds are largely items of commerce.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene 4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile./methyl acrylate; mixtures of high impact strength from styrene copolymers and another polymer, such as, for example, from a polyacrylate, a diene polymer or an ethylene/propylene/diene terpolymer and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers 10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,-a-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid di-octadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino) -s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy -3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl) -hexamethylenediamine
N,N'-di-(3,5-di-tert-butyl-4-hydroxyphenylpropionyl) -trimethylenediamine
N,N'-di-(3,5-di-tert-butyl-4-hydroxyphenylpropionyl) -hydrazine 2. UV absorbers and light stabilizers
2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis -(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p- methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-striazine; 2,4-bis(2,4-dihydroxyphenyl)-6-(4-chlorophenyl) -s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy -4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoyyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tertbutyl -4-hydroxyphenylpropionyl)-hydrazine, 3-salicyloylamino -1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexa.decyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flame proofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans: and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H.F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H.F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single coat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, and 3',5'-di-tert-amyl derivatives.

(b) 2-Hydroxy-benzophenones, for example, the 4-hydyroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

(c) Acrylates, for example, alpha-cyano-$\beta$,$\beta$-diphenylacrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-4-(1,1,3,3-tetramethylbutyl)-phenol], such as the 1:1 or 1:2 complex, optionally with additional ligands such as n-butylamine, triethanolamine or N-cyclo-hexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-di-methylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa(ethyleneoxy)carbonyl)-ethylphenyl]-2H-benzotriazole, dodecylated 2-(2-hydroxy-5-methylphenyl)-2H-benzotriazole, 2-[2-hydroxy-3-tert-butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alphadimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-

[2-hydroxy-3-tert-butyl-5-(2-octyloxycarbonyl)ethyl-phenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising
(a) an acid catalyzed thermoset coating or enamel based on hot crosslinkable acrylic, polyester or alkyd resins,
(b) a NOR$_1$-substituted 2,2,6,6-tetraalkylpiperidine compound, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of Phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl) pentaerythritol diphosphite, tristearyl-sorbitol triphosphite, tetrakis-(2,4-di-tert.butylphenyl)-4,4-diphenylylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

2,4-Bis[N,N-bis(1-cyclohexyloxy-2,2,6,6-tetramethyl-piperidin-4-yl)amino]-6-(N,N-dioctadecylamino)-s-triazine A solution of 70% aqueous tert-butyl hydroperoxide (15.5 grams) in cyclohexane is heated at reflux using a Dean-Stark apparatus for three hours to remove water. The solution is then added to 0.2 gram of molybdenum trioxide and 13.7 grams of 2,4-bis[N,N-bis(2,2,6,6-tetramethylpiperidin-4-yl)amino]-6-(N,N-dioctadecylamino)-s-triazine in a Fischer-Porter pressure bottle. After heating the reaction mixture for six hours at 140° C., the mixture is stirred with aqueous sodium sulfite. The organic phase is separated, washed with brine, dried over anhydrous magnesium sulfate and concentrated under reduced pressure. Purification using liquid chromatography affords the title compound as a white foam.

Analysis:
Calcd for $C_{99}H_{186}N_{10}O_4$: C, 75.2; H, 11.9; N, 8.9.
Found: C, 75.4; H, 12.2; N, 8.9.

EXAMPLE 2

2,4-Bis[N,N-bis(1-octyloxy-2,2,6,6-tetramethylpiperidin-4-yl)amino-6-chloro-s-triazine A solution of 10.0 grams of 2,4-bis[N,N-bis(2,2,6,6-tetramethylpiperidin-4-yl)amino]-6-chloro-s-triazine in 100 ml of n-octane containing suspended molybdenum trioxide (0.3 gram) is heated at reflux with a Dean-Stark trap in place. A solution of 29.3 grams of 70% aqueous tert-butyl hydroperoxide is added to the reaction mixture dropwise and the water produced is removed azeotropically. The dark orange reaction mixture is heated at reflux till colorless. The insoluble catalyst is removed by filtration and the filtrate concentrated under reduced pressure. The residue is dissolved in ethyl acetate and stirred with saturated aqueous sodium sulfite. The organic phase is separated, dried over anhydrous magnesium sulfate and then evaporated to leave the crude product. Preparative liquid chromatography affords the title compound as a white foam.

EXAMPLE 3

2,4-Bis[N,N-bis(1-octyloxy-2,2,6,6-tetramethylpiperidin-4-yl)amino]-6-n-butylamino-s-triazine A mixture of equimolar quantities of the compound prepared in Example 2, n-butylamine and sodium hydroxide in xylene is heated at reflux for eighteen hours to afford the title compound as a white solid.

EXAMPLE 4

N,N'-Bis[2,4-bis(N,N-bis(1-octyloxy-2,2,6,6-tetramethylpiperidin-4-yl)amino)-s-triazin-6-yl]-hexamethylenediamine Following the general procedure of Example 3 and using appropriate quantities of hexamethylenediamine in place of n-butylamine, the title compound is obtained.

EXAMPLES 5–19

Using the general procedure of the examples above, the following instant compounds are prepared.

| | Compounds of Formula I | |
|---|---|---|
| Example | $R_1$ | $R_2$ and $R_3$ are each |
| 5 | cyclohexyl | tert-octylamino |
| 6 | methyl | tert-octylamino |
| 7 | cyclohexyl | together are morpholino |
| 8 | cyclohexyl | 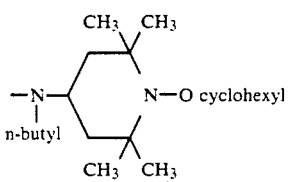 |
| 9 | methyl | same as Example 8 except for —O methyl |
| 10 | cyclohexyl | dodecylthio |
| 11 | cyclohexyl | 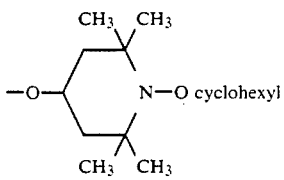 |
| 12 | methyl | same as Example 11 except for O-methyl |
| 13 | methyl | dodecylthio |

Compounds of Formula I, II or III where the s-triazine group contains two

| | $\left[\begin{array}{c}\text{R—O—N}\diagup\diagdown\text{N—}\end{array}\right]_2$ moieties | | | |
|---|---|---|---|---|
| Example of Formula I | R | $R_3$ | | |
| 14 | cyclohexyl | dioctylamino | | |
| 15 | methyl | dioctylamino | | |
| 16 | cyclohexyl | —N(CH$_3$)(CH$_2$)$_3$OC$_4$H$_9$ | | |
| Formula II | R | $T_1$ | | |
| 17 | cyclohexyl | —NH(CH$_2$)$_3$O(CH$_2$)$_2$O(CH$_2$)$_3$NH— | | |
| Formula III | R | $T_2$ | $T_3$ | $T_4$ |
| 18 | cyclohexyl | methyl | tert-butyl | 1,1-butylidene |
| 19 | methyl | hydrogen | hydrogen | 2,2-propylidene |

EXAMPLE 20

N,N'-Bis[2,4-di[bis(2-octyloxy-2,2,6,6-tetramethylpiperidin-4-yl)amino]-s-triazine-6-yl]-1,6-hexanediamine The title compound is prepared by the reaction of bis(1-octyloxy-2,2,6,6-tetramethylpiperidin-4-yl)amine with N,N'-bis(2,4-dichloro-s-triazin-6-yl)-1,6-hexanediamine.

EXAMPLE 21

N,N',N'',N'''-Tetrakis[2,4-di[bis(1-octyloxy-2,2,6,6-tetramethylpiperidin-4-yl)amino]-s-triazin-6-yl]-N,N'-bis(3-aminopropyl)-ethylenediamine The title compound is prepared by the reaction of 6-chloro-2,4-di[bis(1-octyloxy-2,2,6,6-tetramethylpiperidin-4-yl)amino]-s-triazine with N,N'-bis(3-aminopropyl)ethylenediamine.

EXAMPLE 22

2,4-Bis[N,N-bis(1-cyclohexyloxy-2,2,6,6-tetramethylpiperidin-4-yl)amino]-6-chloro-s-triazine A solution of 25.0 grams of 2,4-bis[N,N-bis(2,2,6,6-tetramethylpiperidin-4-yl)amino]-6-chloro-s-triazine in 160 ml of cyclohexane containing suspended molybdenum trioxide (0.82 gram) is heated at reflux with a Dean-Stark trap in place. A solution of 110.0 grams of tert-butyl hydroperoxide (70% aqueous solution) is added to the reaction mixture at 70° C. over a two-hour period, and the water produced is removed azeotropically. The dark orange reaction mixture is transferred into a pressure bottle and heated at 150° C. for four hours till the reaction mixture is colorless. An insoluble residue is removed by filtration, and the filtrate concentrated under reduced pressure. The resulting residue is dissolved in ethyl acetate and stirred with aqueous sodium sulfite. The organic phase is separated, dried over anhydrous sodium sulfate and evaporated to give the above-named material as a crude product.

Analysis:

Calcd. for $C_{63}H_{112}N_9O_4Cl$: C, 69.1; H, 10.3; N, 11.5; Cl, 3.2.

Found: C, 69.1; H, 10.8; N, 10.9; Cl, 3.4.

EXAMPLE 23

N,N'-Bis[2,4-bis[N,N-bis(1-cyclohexyloxy-2,2,6,6-tetramethylpiperidin-4-yl)amino]-s-triazin-6-yl]-N,N'-dimethylhexamethylenediamine A solution of 11.0 grams of the compound prepared in Example 22, 0.72 gram of N,N'-dimethylhexamethylenediamine, 0.4 gram of sodium hydroxide in 100 ml of o-xylene is heated at reflux with a Dean-Stark trap in place. After eight hours, the reaction mixture is concentrated under reduced pressure, and the residue is purified by flash chromatography to afford the title compound as a white solid.

Analysis:

Calc. for $C_{134}H_{242}N_{20}O_8$: C, 71.2; H, 10.8; N, 12.4.

Found: C, 71.6; H, 11.2; N, 12.1.

EXAMPLE 24

Light Stabilization of Polypropylene

This example illustrates the light stabilizing effectiveness of instant stabilizers.

Polypropylene powder (Himont Profax 6501) stabilized with 0.2% by weight of n-octadecyl 3,5-di-tertbutyl-4-hydroxyhydrocinnamate is thoroughly blended with the indicated amount of additive. The blended materials are then milled on a two-roll mill at 182° C. for five minutes, after which time the stabilized polypropylene is sheeted from the mill and allowed to cool. The milled polypropylene is then cut into pieces and compression molded on a hydraulic press at 250° C. and 175 psi (1.2×10⁶ Pa) into 5 mil (0.127 mm) films. The sample is exposed in a fluorescent sunlight/black light chamber until failure. Failure is taken as the hours required to reach 0.5 carbonyl absorbance by infrared spectroscopy on the exposed films.

| Additive Compound of | Additive Concentration (% by weight) | FS/BL Test Results (hours to Failure) |
|---|---|---|
| Base Resin | — | 340 |
| Example 1 | 0.1 | 1070 |

Additionally the instant compounds protect polyolefins against gas fading when said polymers are exposed to natural gas.

EXAMPLE 25

Stabilization of High Solids Thermoset Acrylic Resin Enamel

A thermoset acrylic enamel based on a binder of 70% by weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.4B cm) panels (Uniprime from Advanced Coatings Technology) are spray coated with a silver metallic base coat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 4 hours under UV light at 70° C. The panels are exposed in the QUV for 1500 hours. The 20° gloss values of the panels are determined before and after exposure.

The loss of gloss of the stabilized panels is considerably less than that of the unstabilized control panels.

EXAMPLE 26

N,N'-Bis[2,4-bis[N,N-bis(1-octyloxy-2,2,6,6-tetramethylpiperidin-4-yl)amino]-s-triazin-6-yl]-N,N'-dimethylhexamethylenediamine Following the procedure of Example 23 using appropriate quantities of the compound of Example 2 and N,N'-dimethylhexamethylenediamine with sodium hydroxide in o-xylene, the title compound is obtained as a white resin.

Analysis:
Calcd for $C_{150}H_{290}N_{20}O_8$: C, 72.0; H, 11.7; N, 11.2.
Found: C, 72.0; H, 11.6; N, 10.9.

What is claimed is:

1. A compound having formula II

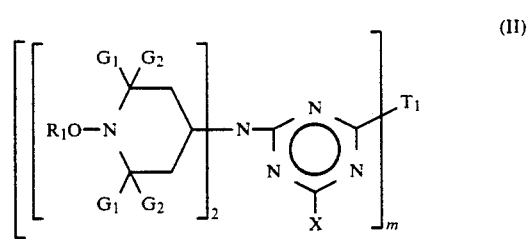

$G_1$ and $G_2$ are independently alkyl of 1 to 4 carbon atoms, or $G_1$ and $G_2$ together are pentamethylene,
$R_1$ is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl;
X is $-SR_5$, $-NR_6R_7$, $-NR_8-R_9-NR_{10}R_{11}$, $-OR_4$, $-O(-R_{12}O)_nR_{13}$,

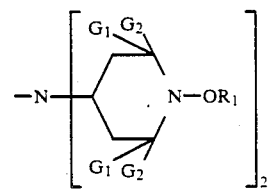

or

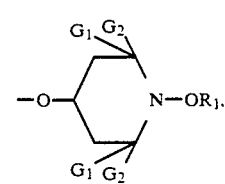

$R_4$ has the same meaning as $R_1$,
$R_5$ has the same definitions as $R_1$ and additionally $R_5$ is alkyl of 2 to 4 carbon atoms substituted by hydroxy, by alkoxy of 1 to 12 carbon atoms or by di($C_1$-$C_4$-alkyl)amino,
$R_6$ and $R_8$ are independently hydrogen, alkyl of 1 to 18 carbon atoms, cycloalkyl of 5 to 12 carbon atoms, aralkyl of 7 to 15 carbon atoms or alkyl of 2 to 4 carbon atoms substituted by hydroxy, by alkoxy of 1 to 12 carbon atoms or by

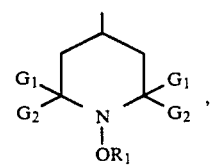

$R_7$ has the same meaning as $R_6$ or $R_6$ and $R_7$ together with N-atom to which they are linked for a 5-7 membered heterocyclic ring containing one or two nitrogen atoms or oxygen,

R₉ is alkylene of 2 to 12 carbon atoms,

R₁₀ and R₁₁ have independently of the same definition as R₆ or R₁₀ and R₁₁ together have the same definition as R₆ and R₇ together.

R₁₂ is alkylene of 2 to 4 carbon atoms,

R₁₃ is hydrogen, alkyl of 1 to 18 carbon atoms, phenyl or said phenyl substituted by alkyl of 1 to 12 carbon atoms or by

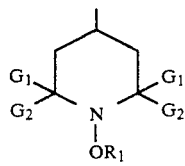

n is an integer of 2 to 20, m is an integer of 2 to 4,

T₁ is piperazinyl,

—NR₁₄—(CH₂)ₐO(CH₂)ᵦO(CH₂)ₐNR₁₄—, —NR₁₄—(CH₂) or

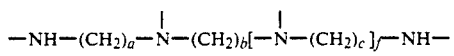

wherein

R₁₄ is hydrogen, alkyl of 1 to 18 carbon atoms, cycloalkyl of 5 to 12 carbon atoms, aralkyl of 7 to 15 carbon atoms, alkanoyl of 2 to 18 carbon atoms, alkenoyl of 3 to 5 carbon atoms or benzoyl, a, b, c, d are independently 2 or 3, f is 0 or 1.

2. A compound according to claim 1 wherein G₁ and G₂ are each methyl.

3. A compound according to claim 1 wherein R₁ is alkyl of 1 to 12 carbon atoms, cyclohexyl or alpha-methylbenzyl.

4. A compound according to claim 3 wherein R₁ is methyl, heptyl, octyl, nonyl, cyclohexyl or alpha-methylbenzyl.

5. A compound according to claim 1 wherein R₅ is alkyl of 1 to 18 carbon atoms,

6. A compound according to claim 1 wherein R₆ is hydrogen, alkyl of 1 to 18 carbon atoms, or a group

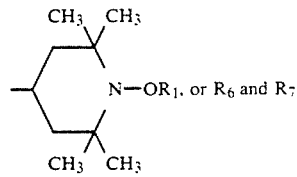

together with the nitrogen atom to which they are attached are morpholino.

7. A compound according to claim 1 wherein T₁ is

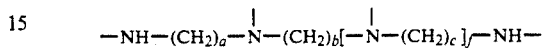

8. The compound according to claim 1 which is N,N'-bis[2,4-bis[N,N-bis(1-cyclohexyloxy-2,2,6,6-tetramethylpiperidin-4-yl)amino]-s-triazin-6-yl]-N,N'-dimethylhexamethylenediamine.

9. The compound according to claim 1 which is N,N'-Bis[2,4-bis[N,N-bis(1-octyloxy-2,2,6,6-tetramethylpiperidin-4-yl)amino]-s-triazin-6-yl]-N,N'-dimethylhexamethylenediamine.

10. A composition stabilized against the deleterious effects of actinic light which comprises
    (a) a synthetic polymer, and
    (b) an effective stabilizing amount of a compound according to claim 1.

11. A composition according to claim 10 wherein the polymer is a polyolefin.

12. A composition according to claim 11 wherein the polyolefin is polypropylene.

13. A composition according to claim 10 wherein the polymer is a coating system based on alkyd, acrylic, acrylic alkyd, polyester, epoxide, urethane, polyamide, vinyl or epoxy-polyester resins.

14. A composition according to claim 13 which contains a UV absorber or additional light stabilizer.

15. A method for stabilizing a synthetic polymer against oxidative, thermal or actinic degradation which comprises incorporating into said organic material an effective stabilizing amount of a compound according to claim 1.

16. 2,4-Bis[N,N-bis(1-octyloxy-2,2,6,6-tetramethylpiperidin-4-yl)amino]-6-chloro-s-triazine.

17. 2,4-Bis[N,N-bis(1-cyclohexyloxy-2,2,6,6-tetramethylpiperidin-4-yl)amino]-6-chloro-s-triazine.

18. A composition according to claim 13 wherein component (b) is N,N'-bis[2,4-bis[N,N-bis(1-cyclohexyloxy -2,2,6,6-tetramethylpiperidin-4-ylamino]-s-triazin-6-yl]-N,N'-dimethylhexamethylenediamine or N,N'-bis[2,4-bis[N,N-bis(1-octyloxy -2,2,6,6-tetramethylpiperidin-4-ylamino]-s-triazin-6-yl]-N,N'-dimethyl-hexamethylenediamine.

* * * * *